(12) United States Patent
Cardola et al.

(10) Patent No.: US 6,248,705 B1
(45) Date of Patent: Jun. 19, 2001

(54) STABLE PERFUMED BLEACHING COMPOSITIONS

(75) Inventors: Sergio Cardola, Rome (IT); Lucio Pieroni, Brussels (BE); Raffaele Scoccianti, Rome (IT)

(73) Assignee: The Procter & Gamble Company, Cincinnati, OH (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/101,570

(22) PCT Filed: Jan. 8, 1997

(86) PCT No.: PCT/US97/00243

§ 371 Date: Jul. 13, 1998

§ 102(e) Date: Jul. 13, 1998

(87) PCT Pub. No.: WO97/25396

PCT Pub. Date: Jul. 17, 1997

(30) Foreign Application Priority Data

Jan. 12, 1996  (EP) .................................................. 96870001

(51) Int. Cl.⁷ ................................ C11D 3/50; C11D 7/08; C11D 3/39; C11D 1/62; C11D 1/75
(52) U.S. Cl. .......................... 510/191; 510/101; 510/102; 510/103; 510/199; 510/238; 510/253; 405/463; 405/503; 405/504; 405/302; 405/309; 405/362
(58) Field of Search ..................... 510/101, 102, 510/103, 191, 199, 238, 253, 405, 463, 503, 504, 302, 309, 362

(56) References Cited

U.S. PATENT DOCUMENTS

| | | | |
|---|---|---|---|
| 3,867,101 | 2/1975 | Herring | 23/267 |
| 4,229,410 | 10/1980 | Kosti | 422/28 |
| 4,396,522 | 8/1983 | Callicott et al. | 252/163 |
| 4,666,622 | * 5/1987 | Martin et al. | 252/99 |
| 4,781,854 | * 11/1988 | Overton et al. | 252/100 |
| 4,842,771 | 6/1989 | Rorig et al. | 252/547 |
| 4,852,201 | * 8/1989 | Wundrock et al. | 15/145 |
| 4,874,536 | 10/1989 | Strickland, Jr., et al. | 252/90 |
| 4,891,150 | 1/1990 | Gross et al. | 252/142 |
| 4,923,631 | 5/1990 | Sims et al. | 252/186.42 |
| 5,061,393 | * 10/1991 | Linares et al. | 252/143 |
| 5,078,896 | 1/1992 | Rorig et al. | 252/102 |
| 5,149,463 | 9/1992 | Peterson | 252/301.21 |
| 5,384,063 | * 1/1995 | Woo et al. | 252/142 |
| 5,403,587 | 4/1995 | McCue et al. | 424/195.1 |
| 5,602,090 | 2/1997 | Melikyan et al. | 510/372 |
| 5,698,041 | * 12/1997 | Woo et al. | 134/3 |

FOREIGN PATENT DOCUMENTS

| | | | |
|---|---|---|---|
| 0 288 689 A2 | 11/1988 | (EP) | C11D/3/48 |
| 0 598 694 B1 | 5/1994 | (EP) | C11D/3/39 |
| WO 88/00795 | 7/1986 | (WO) | A01N/65/00 |
| WO 95/15495 | 11/1993 | (WO) | G01N/33/53 |

\* cited by examiner

Primary Examiner—Yogendra Gupta
Assistant Examiner—Charles Boyer
(74) Attorney, Agent, or Firm—Jason J. Camp

(57) ABSTRACT

Stable, perfumed, highly acidic liquid compositions are disclosed which comprise a source of active oxygen, a surfactant and a cyclic terpene/sesquiterpene compound (e.g. eucalyptol). Said compositions are particularly suitable to clean hard surfaces like toilet bowls.

28 Claims, No Drawings

US 6,248,705 B1

STABLE PERFUMED BLEACHING COMPOSITIONS

TECHNICAL FIELD

The present invention relates to bleaching compositions, more particularly to stable perfumed acidic liquid compositions comprising a source of active oxygen. Said compositions are particularly suitable for the bleaching and cleaning of hard-surfaces including toilet bowls and the like.

Background

A great variety of bleaching and cleaning compositions have been described in the art. Bleaching/cleaning compositions comprising a source of active oxygen and being formulated at low pH are particularly interesting for the cleaning of hard-surfaces, especially for the hygienic cleaning of sanitary fittings such as toilet bowls and the like.

A drawback associated with liquid compositions comprising a source of active oxygen, and more particularly with liquid compositions comprising a source of active oxygen and being formulated at low pH, is that it is quite difficult to stably incorporate perfumes therein. Indeed, traditional perfumes are usually made by a blend of components including esters, chetones, aldehydes and the like. Said perfumes are sensitive to sources of active oxygen and/or to low pH. In other words, said perfumes show significant instability in liquid compositions comprising a source of active oxygen like persulphate salts or hydrogen peroxide, especially when formulated in highly acidic conditions.

Indeed, such perfumes are easily hydrolysed in the presence of low pH, especially at pH below 2. The result of such hydrolysis is that perfumes lose their original fragrance/smell.

Such perfumes like, for example, those commercially available from Dragoco under the name of Ultra clean plus® or Givaudian-Roure®, are easily oxidised by sources of active oxygen, leading thereby to a loss of the total amount of active perfumes resulting in a loss of their original fragrance/smell as well as to a loss of the total amount of active oxygen which would otherwise be available to perform its bleaching action on the surfaces to be treated.

In fact, bleaching species, like hydrogen peroxide and/or persulphate, not only decompose perfume components upon an oxidation mechanism, but also decompose themselves in the presence of perfumes, therefore leading to a lowering of the total level of the bleach in a liquid composition and especially in a highly acidic liquid composition, with consequent performance issues and chemical stability issues upon long storage periods.

It is therefore an object of the present invention to provide perfumed liquid compositions, especially perfumed highly acidic liquid compositions comprising a source of active oxygen which are chemically stable for long storage periods.

It is another object of the present invention to provide perfumed highly acidic liquid compositions comprising a source of active oxygen which deliver improved scent.

It is yet another object of the present invention to provide perfumed highly acidic liquid compositions comprising a source of active oxygen which deliver improved bleaching performance.

The present invention meets the above objects by incorporating a cyclic terpene/sesquiterpene perfume selected from the group of eucalyptol, cedrol, pinocarveolus, sesquiterpenic globulul alcohol and mixtures thereof, in an acidic liquid composition having a pH below 2, and comprising a source of active oxygen and a surfactant. More particularly, it has been found that said cyclic terpene/sesquiterpene perfumes and especially eucalyptol are insensitive to pH, especially highly acidic pH and to sources; of active oxygen. Thus, by incorporating such a perfume into a highly acidic liquid composition comprising a source of active oxygen and a surfactant excellent chemical stability is obtained upon long storage periods as well as improved scent and/or improved bleaching performance, as compared to the same composition but with another perfume, like, for instance, traditional blends of components like Ultra Clean Plus® commercially available from Dragoco. Indeed, the chemical decomposition of a source of active oxygen present in a liquid composition, especially in a highly acidic liquid composition, is reduced in the presence of said cyclic terpene/sesquiterpene perfumes like eucalyptol, as compared to other perfumes like Ultra Clean Plus® commercially available from Dragoco.

An advantage associated with the compositions of the present invention comprising said cyclic terpene/sesquiterpene perfumes like eucalyptol is that good bacterial performance is delivered. Indeed, the incorporation of said cyclic terpene/sesquiterpene perfumes like eucalyptol in for example a highly acidic liquid composition comprising a source of active oxygen and a surfactant, allows to reduce the total level of source of active oxygen necessary in said liquid composition to deliver a given disinfection performance as compared to the same composition but without said cyclic terpene/sesquiterpene perfumes like eucalyptol.

Another advantage of the incorporation of said cyclic terpene/sesquiterpene perfumes like eucalyptol in highly acidic liquid compositions comprising a source of active oxygen and a surfactant, is that said compositions may be easily formulated as thickened compositions. Indeed, it has been found that said cyclic terpene/sesquiterpene perfumes and especially eucalyptol have a minimal impact on viscosity. In other words, they allow to formulate stable perfumed acidic liquid compositions comprising a source of active oxygen and a surfactant, that still have high viscosity, despite the presence of perfumes, even at high levels. In fact, traditional perfumes like Ultra Clean Plus® commercially available from Dragoco, especially at high levels of said perfumes, are known to have a. general tendency to significantly decrease composition viscosity by changing laminar/micellar aggregation.

Furthermore, said cyclic terpene/sesquiterpene perfumes like eucalyptol are easily dissolved in water based matrix like the acidic liquid compositions of the present invention upon dissolution of low levels of surfactants. For example, when formulating the present compositions as thickened compositions, lower levels of cationic surfactants are needed to stably incorporate said cyclic terpene/sesquiterpene perfumes in the compositions herein while providing the desired viscosity to said compositions. In other words, the incorporation of such a cyclic terpene/sesquiterpene perfume, in a perfumed highly acidic liquid bleaching composition allows to achieve optimum rheology for hard-surfaces applications including vertical hard-surface applications with less surfactants than would otherwise be required with the presence of other perfumes instead of said perfume according to the present invention. This results in another advantage of the present invention which is the ease of spread and rinse of the compositions herein when applied on hard-surfaces. In fact, poor product rinsing is driven by the crystallisation of the layers of surfactants like cationic surfactants deposited onto a hard-surface, e.g. toilet blows. Once crystals are formed, they tightly encrust on the surface and cannot be easily removed without mechanical help, e.g. friction and/or rubbing. The use of said cyclic terpene/sesquiterpene perfumes like eucalyptol as the perfume to be incorporated in a perfumed highly acidic liquid bleaching composition allows the use of lower levels of surfactants like cationic surfactants, preventing and/or minimising thereby the crystal growth, and thus facilitating its rinse, this even after overnight application of said composition on a toilet bowl.

Yet another advantage is that the stable perfumed acidic liquid compositions of the present invention are efficient on various surfaces to clean various soils and stains. Additionally, said compositions, when used to treat hard-surfaces, especially toilet bowls, exhibit outstanding soil discoloration, soil solubilization and emulsification properties together with a germicidal action, this when used both neat or diluted.

EP-A-188 025 discloses liquid stable thickened low-pH bleaching compositions comprising an inorganic peroxy compound, a strong acid and a thickening surfactant. In EP-A-188 025 the thickening surfactant is; selected from (1) amine oxides wherein at least one of the hydrocarbon groups linked to the nitrogen is a linear or branched alkyl group of C6 to C18 carbon atoms, preferably C12 to C18, (2) amines and (3) quatemaary ammonium salts wherein at least one of the hydrocarbon groups linked to the nitrogen is a linear or branched alkyl group of C8 to C18 carbon atoms. No cyclic terpene/sesquiterpene perfumes are disclosed.

EP-A-598 694 discloses acidic compositions (pH=0–4) comprising persulfate salts and nonionic surfactants which are suitable to clean toilet bowls. No cyclic terpene/sesquiterpene perfumes are disclosed.

WO 95/15495 disclosesacidic thickened aqueous compositions comprising persulfate salts and a surfactant thickening system comprising a quatemary ammonium compound together with a short chain amine oxide. Said compositions are suitable to clean hard-surfaces including toilet bowls. No cyclic terpene/sesquiterpene perfumes are disclosed.

U.S. Pat. No. 5,403,587 discloses liquid antimicrobial compositions which can be used to sanitise, disinfect, and clean hard-surfaces. More particularly, said patent discloses liquid compositions (pH 1 to 12) comprising essential oils which exhibit antimicrobial properties efficacy (0.02% to 5%) such as eucalyptus. Said compositions may further comprise other antimicrobial ingredients like phenolic compounds, quatemary ammonium compounds. No source of active oxygen is disclosed.

SUMMARY OF THE INVENTION

The present invention encompasses a perfumed acidic liquid bleaching composition having a pH below 2, and comprising a source of active oxygen, a surfactant and a cyclic terpene/sesquiterpene perfume selected from the group of eucalyptol, cedrol, pinocarveolus, sesquiterpenic globulul alcohol and mixtures thereof.

The present invention also encompasses a process of treating hard-surfaces, especially toilet bowls, wherein a perfumed acidic liquid composition according to the present invention, is used.

DETAILED DESCRIPTION OF THE INVENTION

The compositions of the present invention are acidic compositions. In order to obtain appropriate stability of the source of active oxygen in the compositions according to the present invention, said compositions are formulated at a pH bellow 2, preferably at a pH between 0 and 1, more preferably at a pH between 0 and 0.7, and most preferably at a pH between 0 and 0.5. Acidity further contributes to formulate compositions according to the present invention which exhibit good limescale removing performance while exhibiting also good disinfecting properties. Accordingly, the compositions of the present invention comprise organic and/or inorganic acids. Particularly suitable organic acids to be used herein are aryl and/or alkyl sulfonate, such as methane sulfonic acids, citric acid, succinic acid, sulphamic acid and the like. Particularly suitable inorganic acids are sulfuric, phosphoric, nitric acids and the like.

The compositions according to the present invention comprise, as an essential ingredient, a source of active oxygen, or mixtures thereof. The source of active oxygen according to the present invention acts as an oxidising agent, it increases the ability of the compositions to remove colored stains and organic stains in general, to destroy malodorous molecules and to kill germs. Suitable sources of active oxygen for use herein are water-soluble sources of hydrogen peroxide including persulfate, dipersulphate, persulfuric acid, percarbonates, metal peroxides, perborates, persilicate salts, and mixtures thereof, as well as hydrogen peroxide, and mixtures thereof. As used herein a hydrogen peroxide source refers to any compound which produces hydrogen peroxide when said compound is in contact with water.

In addition, other classes of peroxides can be used as an alternative to hydrogen peroxide and sources thereof or in combination with hydrogen peroxide and sources thereof. Suitable classes include dialkylperoxides., diacylperoxides, preformed percarboxylic acids, organic and inorganic peroxides and/or hydroperoxides.

Suitable organic peroxides/hydroperoxides include diacyl and dialkyl peroxides/hydroperoxides such as dibenzoyl peroxide, t-butrl hydroperoxide, dilauroyl peroxide, dicumyl peroxide, and mixtures thereof Suitable preformed peroxyacids for use in the compositions according to the present invention include diperoxy-dodecandloic acid DPDA, magnesium perphthalic acid, perlauric acid, perbenzoic acid, diperoxyazelaic acid and mixtures thereof.

Persulfate salts, or mixtures thereof, are the preferred sources of active oxygen to be used in the compositions according to the present invention. Preferred persulfate salt to be used herein is the monopersulfate triple salt. One example of monopersulfate salt commercially available is potassium monopersulfate commercialised by Peroxide Chemie GMBH under the trade name Curox®. Other persulfate salts such as dipersulfate salts commercially available from Peroxide Chemie GMBH can be used in the compositions according to the present invention.

The compositions according to the present invention comprise from 0.1% to 30% by weight of the total composition of said source of active oxygen, or mixtures thereof, preferably from 0.1% to 20%, more preferably from 1% to 10%, and most preferably from 1% to 7%.

The compositions according to the present invention comprise, as an essential ingredient, a cyclic terpene/sesquiterpene perfume selected from the group of eucalyptol, cedrol, pinocarveolus, sesquiterpenic globulul alcohol and mixtures thereof.

Eucatyptol (1,8-cyneol) is highly preferred herein as said cyclic terpene/sesquiterpene perfume. Eucalyptol may be available per se as a raw material as well as in the form of essential oil of eucalyptus. Examples of eucalyptol to be used herein is the one commercially available under the trade name Eucalyptol® from Garcia, Bordas, or Selin.

The compositions according to the present invention comprise from 0.01 to 5% by weight of the total composition of said cyclic, terpene/sesquiterpene perfume, preferably from 0.01% to 3%, more preferably from 0.01 to 1%, and most preferably from 0.1% to 0.5%.

The compositions according to the present invention comprise, as an essential ingredient, a surfactant, or mixtures thereof. Said surfactants help the stable incorporation of said cyclic terpene/sesquiterpene perfume in the highly acidic liquid bleaching compositions of the present invention. The presence of said surfactants in the perfumed highly acidic liquid bleaching compositions of the present invention also allows to provide good cleaning performance on different types of stains including bleachable stains like tea, grass, enzymatic stains like blood, greasy stains like barbecue sauce, spaghetti sauce, bacon grease and the like. The presence of said surfactants in the compositions herein may also allow to provide compositions with desired viscosity by appropriately chosen surfactants and levels thereof. Indeed, in a preferred embodiment according to the present invention the compositions herein are thickened. Such thickened compositions are desirable since the compositions herein are preferably used on inclined surfaces such as bath tubs, sinks or toilet bowls. Thickened compositions have a better cling onto inclined surfaces, thus a longer residence time for the compositions to remove for example mineral encrustations. The thickened compositions according to the present invention have preferably a viscosity of more than 100 cps at 20° C., more preferably of from 150 cps to 1500 cps, and most preferably of from 250 cps to 900 cps, when measured with a Brookfield viscometer at 60 rpm with a spindle n° 2 or with the Carri-med rheometer at 50 dyne/cm2.

All types of surfactants may be used in the present invention including nonionic, anionic, cationic, amphoteric or zwitterionic surfactants. It is also possible to use mixtures of such surfactants without departing from the spirit of the present invention.

Accordingly, the compositions according to the present invention comprise up to 50% by weight of the total composition of a surfactant, or mixtures thereof, preferably of from 0.1% to 20%, more preferably of from 1% to 10%, and most preferably of from 1% to 5%.

Preferred surfactants to be used herein are the cationic surfactants, or mixtures thereof. This is because they have better hard-surface substantivity/affinity resulting thereby in better cling onto said surface (hard-surfaces are typically made by layers of anionic species like silicates and/or alluminates). Said cationic surfactants have also excellent stability even at the lowest pH. Suitable cationic surfactants to be used herein include derivatives of quatemary ammonium, phosphonium, imidazolium and sulfonium compounds. Preferred cationic surfactants for use herein are quaternary ammonium compounds wherein one or two of the hydrocarbon groups linked to nitrogen are a saturated, linear or branched alkyl group of 6 to 30 carbon atoms, preferably of 10 to 25 carbon atoms, and more preferably of 12 to 20 carbon atoms, and wherein the other hydrocarbon groups (i.e. three when one hydrocarbon group is a long chain hydrocarbon group as mentioned hereinbefore or two when two hydrocarbon groups are long chain hydrocarbon groups as mentioned hereinbefore) linked to the nitrogen are independently substituted or unsubstituted, linear or branched, alkyl chain of from 1 to 4 carbon atoms, preferably of from 1 to 3 carbon atoms, and more preferably are methyl groups. In the preferred embodiment of the present invention where persulfate salts or mixtures thereof are used as sources of active oxygen, the quaternary ammonium compound is preferably a non-chloride/non halogen quatemary ammonium compound. The counterion used in said quatemary ammonium compounds are compatible with any source of active oxygen and are selected from the group of methyl sulfate, or methylsulfonate, and the like.

Particularly preferred to be used in the compositions of the present invention are trimethyl quatemary ammonium compounds like myristyl trimethylsulfate, cetyl trimethylsulfate and/or tallow trimethylsulfate. Such trimethyl quatemary ammonium compounds are commercially available from Hoechst, or from Albright & Wilson under the trade name EMPIGEN CM®.

Suitable amphoteric surfactants to be used in the compositions according to the present invention include amine oxides having the following formula $R_1R_2R_3NO$ wherein each of R1, R2 and R3 is independently a saturated substituted or unsubstituted, linear or branched alkyl groups of from 1 to 30 carbon atoms, preferably of from 6 to 30 carbon atoms, more preferably ol from 10 to 20 carbon atoms, and most preferably of from 8 to 18 carbor, atoms. Suitable amine oxides for use herein are preferably compatible with source of active oxygen. Preferred amine oxides for use herein are for instance natural blend C8–C10 amine oxides as well as C12–C16 amine oxides commercially available from Hoechst.

In one embodiment of the present invention where the compositions according to the present invention are thickened, quatemary ammonium and short chain amine oxide are preferably used as the thickening system.

Suitable short chain amine oxides to be used according to the present invention are amine oxides having the following formula $R_1R_2R_3NO$ wherein R1 is a C6 to C10 alkyl group, preferably a C8 to C10 alkyl group and wherein R2 and R3 are independently substituted or unsubstituted, linear or branched alkyl groups of from 1 to 4 carbon atoms, preferably of from 1 to 3 carbon atoms, and more preferably are methyl groups. R1 may be a saturated linear or branched alkyl group. Suitable short chain amine oxides for use herein are preferably compatible with any source of active oxygen. Preferred short chain amine oxides for use herein are for instance natural blend C8–C10 amine oxides available from Hoechst.

In the embodiment of the present invention where the thickening system used is said quaternary ammonium compound and said short chain amine oxide, the total level of thickening system to be used in a given perfumed liquid acidic composition comprising a source of active oxygen depends on the thickening desired for said composition, said level being lower than 20%, preferably between 0.1% and 10%, more preferably between 0.1% nad 2% and 5%, and most preferably between 0.1% and 2%.

Suitable nonionic surfactants to be used herein are alkoxylated fatty alcohol nonionic surfactants which can be readily made by condensation processes which are well known in the art. Indeed, a great variety of such alkoxylated fatty alcohols are commercially available which have very different HLB values. The HLB values of such alkoxylated nonionic surfactants depend essentially on the chain length of the fatty alcohol, the nature of the alkoxylation and the degree of alkoxylation. Hydrophilic nonionic surfactants tend to have a high degree of alkoxylation and a short chain fatty alcohol, while hydrophobic surfactants tend to have a low degree of alkoxylation and a long chain fatty alcohol.

Surfactants catalogues are available which list a number of surfactants including nonionics, together with their respective HLB values.

Accordingly, preferred alkoxylated alcohols for use herein are nonionic surfactants according to the formula RO(E)e(P)pH where R is a hydrocarbon chain of from 2 to 24 carbon atoms, E is ethylene oxide and P is propylene oxide, and e and p which represent the average degree of, respectively ethoxylation and propoxylation, are of from 0 to 24. The hydrophobic moiety of the nonionic compound can be a primary or secondary, straight or branched alcohol having from 8 to 24 carbon atoms. Preferred nonionic surfactants for use in the compositions according to the invention are the condensation products of ethylene oxide with alcohols having a straight alkyl chain, having from 6 to 22 carbon atoms, wherein the degree of ethoxylation is from 1 to 15, preferably from 5 to 12. Such suitable nonionic surfactants are commercially available from Shell, for instance, under the trade name Dobanol® or from Shell under the trade name Lutensol®. These nonionics are preferred because they have been found to allow the formulation of a stable product without requiring the addition of stabilisers or hydrotopes. When using other nonionics, it may be necessary to add hydrotopes such as cumene sulphonate or solvents such as butyldiglycolether.

Particularly suitable anionic surfactants are alkyl-diphenyl-ether-sulphonates and alkyl-carboxylates. Other, suitable anionic surfactants herein include water soluble salts or acids of the formula $ROSO_3M$ wherein R is preferably a $C_{10}$–$C_{24}$ hydrocarbyl, preferably an alkyl or hydroxyalkyl having a $C_{10}$–$C_{20}$ alkyl component, more preferably a $C_{12}$–$C_{18}$ alkyl or hydroxyalkyl, and M is H or a cation, e.g., an alkali metal cation (e.g., sodium, potassium, lithium), or ammonium or substituted ammonium (e.g., methyl-, dimethyl-, and trmethyl ammonium cations and quaternary ammonium cations, such as tetramethyl-ammonium and dimethyl piperdinium cations and quaternary ammonium cations derived from alkylamines such as ethylamine, diethylamine, triethylamine, and mixtures thereof, and the like).

Other anionic surfactants useful for detersive purposes can also be used herein. These can include salts (including, for example, sodium, potassium, ammonium, and substituted ammonium salts such as mono-, di- and triethanola-mine salts) of soap, $C_9$–$C_{20}$ linear alkylbenzenesulfonates, $C_8$–C22 primary or secondary alkanesulfonates, $C_8$–$C_{24}$ olefinsulfonates, sulfonated polycarboxylic acids prepared by sulfonation of the pyrolyzed product of alkaline earth metal citrates, e.g., as described in British patent specification No. 1,082,179, $C_8$–$C_{24}$ alkylpolyglycolethersulfates (containing up to 10 moles of ethylene oxide); alkyl ester sulfonates such as $C_{14-16}$ methyl ester sulfonates; acyl glycerol sulfonates, fatty oleyl glycerol sulfates, alkyl phenol ethylene oxide ether sulfates, paraffin sulfonates, alkyl phosphates, isethionates such as the acyl isethionates, N-acyl taurates, alkyl succinamates and sulfosuccinates, monoesters of sulfosuccinate (especially saturated and unsaturated $C_{12}$–$C_{18}$ monoesters) diesters of sulfosuccinate (especially saturated and unsaturated $C_6$–C14 diesters), acyl sarcosinates, sulfates of alkylpolysaccharides such as the sulfates of alkylpolyglucoside (the nonionic nonsulfated compounds being described below), branched primary alkyl sulfates, alkyl polyethoxy carboxylates such as those of the formula $RO(CH_2CH_2O)_kCH_2COO—M^+$ wherein R is a $C_8$–$C_{22}$ alkyl, k is an integer from 0 to 10, and M is a soluble salt-forming cation. Resin acids and hydrogenated resin acids are also suitable, such as rosin, hydrogenated rosin, and resin acids and hydrogenated resin acids present in or derived from tall oil. Further examples are given in "Surface Active Agents and Detergents" (Vol. I and II by Schwartz, Perry and Berch). A variety of such surfactants are also generally disclosed in U.S. Pat. No. 3,929,678, issued Dec. 30, 1975 to Laughlin, et al. at Column 23, line 58 through Column 29, line 23 (herein incorporated by reference).

Preferred anionic surfactants for use in the compositions herein are the alkyl benzene sulfonates, alkyl sulfates, alkyl alkoxylated sulfates, and mixtures thereof. Anionic surfactants provide improved cleaning performance.

The present invention allows to formulate perfumed highly acidic liquid bleaching compositions with excellent chemical stability and/or which deliver improved scent and/or improved bleaching performance.

By "stable" it is meant herein that a composition of the present invention comprising a source of active oxygen or mixtures thereof, such as persulfate salt, preferably does not undergo more than 40% persulfate loss, in 6 months at room temperature (20° C.–25≅ C.). Persulfate concentration can be measured by titration with potassium permanganate after reduction with a solution containing ammonium ferrous sulphate. Said stability test method is well known in the art and is reported, for example, on the technical information sheet of Curox® commercially available from Interox. Alternatively persulfate concentration can also be measured using a chromatography method described in the literature for peracids (F. Di Furia et al., Gas-liquid Chromatography Method for Determination of Peracids, Analyst, Vol 113, May 1988, p 793–795).

It has now been found that by incorporating a cyclic terpene/sesquiterpene perfume selected from the group of eucalyptol, cedrol, pinocarveolus, sesquiterpenic globulul alcohol and mixtures thereof into a highly acidic liquid composition comprising a source of active oxygen and a surfactant excellent chemical stability is obtained upon long storage periods, as compared to the same composition but with another perfume, like, for instance, traditional blends of components like Ultra Clean Plus® commercially available from Dragoco. Indeed, the chemical decomposition of a source of active oxygen present in a liquid composition, especially in a highly acidic liquid composition, is reduced in the presence of said cyclic terpene/sesquiterpene perfumes like eucalyptol, as compared to other perfumes like Ultra Clean Plus® commercially available from Dragoco. Accordingly, in its broadest aspect the present invention encompasses the use of a cyclic terpene/sesquiterpene perfume selected from the group of eucalyptol, cedrol, pinocarveolus, sesquiterpenic globulul alcohol and mixtures thereof, in a liquid composition comprising a source of active oxygen to provide liquid perfumed bleaching compositions with excellent chemical stability that are suitable for bleaching and/or disinfecting surfaces.

By "improved scent" it is meant herein that when measured at a given storage time the loss of the original fragrance/smell of a perfumed acidic liquid composition comprising a source of active oxygen, a surfactant and a cyclic terpene/sesquiterpene perfume according to the present invention is reduced, as compared to the loss of the original fragrance/smell of the same composition but with another perfume like Ultra Clean Plus® commercially available from Dragoco, instead of said cyclic terpene/sesquiterpene perfume according to the present invention.

By "improved bleaching performance" it is meant herein that the perfumed acidic liquid compositions comprising a source of active oxygen, a surfactant and a cyclic terpene/ sesquiterpene perfume according to the present invention allow to provide better bleaching performance than the same compositions but with another perfume like Ultra Clean Plus® commercially available from Dragoco, instead of said cyclic terpene/sesquiterpene perfume according to the present invention.

Also, It has now been found that said cyclic terpene/sesquiterpene perfumes like eucalyptol due to their antimicrobial activity, allow to reduce the total level of source of active oxygen necessary in a given liquid bleaching composition to deliver a given disinfection performance, as compared to the same composition without said cyclic terpene/sesquiterpene perfumes like eucalyptol, as the perfume.

It has further been observed that the incorporation of said cyclic terpene/sesquiterpene perfumes in highly acidic liquid compositions comprising a source of active oxygen and a surfactant, does not interfere on the rheology of said compositions. Indeed, it has been found that said cyclic terpene/sesquiterpene perfumes like eucalyptol have a minimal impact on viscosity. This allows in particular to formulate thickened highly acidic liquid bleaching compositions which are chemically stable upon a prolonged period of time.

The compositions according to the present invention are liquid, preferably aqueous. The compositions according to the present invention comprise from 40% to 99% by weight of the total composition of water, preferably from 60% to 95%, most preferably from 70% to 90%. Deionized water is preferably used.

Depending on the end use envisioned, the compositions according to the present invention may further comprise a variety of other ingredients including dyes, optical brighteners, builders, chelants, pigments, solvents, buffering agents, radical scavengers, polymers, stabilizers and the like.

The present invention further encompasses a process of treating hard-surfaces, especially non-horizontal surfaces like toilet bowls, wherein a composition according to the present invention is used in its neat or diluted form. By "in its diluted form" it is meant herein that said compositions may be diluted with water up to 99% of water. Said dilution may occur either before, after or while said composition is applied to a hard-surface.

The compositions herein find a preferred application in the cleaning of toilet bowls and/or bath tubs. While cleaning toilet bowls compositions according to the present invention may be diluted while or after they are applied to the surface to be cleaned. For example, said compositions may be dispensed from a container onto said hard-surface, then diluted in water and left to act onto said surfaces, then removed by rinsing or flushing.

As used in the foregoing paragraphs, the expression "treating" includes washing as the compositions used in the process according to the present invention comprise surfactants and bleaching as said compositions also comprise a source of active oxygen, preferably persulfate salts.

The present invention is further illustrated by the following examples.

EXAMPLES

The following compositions were made by mixing the listed ingredients in the listed proportions (weight %). All these compositions were chemically stable upon prolonged period of storage, i.e. they did not undergo more than 40% loss when stored at ambient temperature for a period of 6 months. Said compositions also delivered excellent scent upon prolonged storage time and excellent bleaching performance upon use.

|  | #1 | #2 | #3 |
|---|---|---|---|
| Compositions: (weight %) | | | |
| Curox ® | 4 | 4 | 6 |
| C16-quat surfactant | 1.8 | — | 2.5 |
| C16–18 quat surfactant | — | 2.2 | — |
| Eucalyptol | 0.3 | 0.5 | 0.3 |
| pH (trimmed with H2S04) | 0.5 | 0.5 | 0.7 |
| Minors and water | up to 100% | | |
| Viscosity~ (cps at 60 rpm with spindle n°2) | 350 | 400 | 550 | curox® is one of the commercial names of monopersultate salts

|  | #4 | #5 | #6 |
|---|---|---|---|
| Compositions: (weight %) | | | |
| Curox ® | 4 | 6 | 4 |
| C16-quat surfactant | 2.5 | — | 2.5 |
| C16–18 quat surfactant | — | 4.0 | — |
| C8–C12 amine oxides | 0.2 | 0.2 | — |
| Cedrol | — | — | 0.3 |
| Eucalyptus | 0.3 | 0.5 | — |
| pH (trimmed with H2SO4) | 0.7 | 0.5 | 0.7 |
| Minors and water | up to 100% | | |
| Viscosity~ (cps at 60 rpm with spindle n°2) | 400 | 400 | 300 |

What is claimed is:

1. A perfumed acidic liquid composition having a pH of from 0 to 1, and comprising a source of active oxygen, a surfactant, and a cyclic terpene/sesquiterpene perfume selected from the group consisting of eucalyptol, cedrol, pinocarveolus, sesquiterpeaic globulul alcohol, and mixtures thereof.

2. A composition according to claim 1 wherein said source of active oxygen is a hydrogen peroxygen, or a source thereof selected from the group consisting of persulfates, dipersulfates, persulfuric acids, percarbonates, metal peroxides, perborates, persilicate salts, dialkylperoxides, diacylperoxides, preformed percarboxylic acids, organic and inorganic peroxides and/or hydroperoxides and mixtures thereof.

3. A composition according to claim 1 wherein said source of active oxygen is a persulfate salt or mixtures thereof.

4. A composition according to claim 1 wherein said cyclic terpene/sesquiterpene perfuime is eucalyptol.

5. A composition according to claim 1 wherein the level of said source of active oxygen, or mixtures thereof, is from 0.1% to 30% by weight of the total composition.

6. A composition according to claim 5 wherein the level of said source of active oxygen, or mixtures thereof, is from 0.1% to 20% by weight of the total composition.

7. A composition according to claim 5 wherein the level of said source of active oxygen, or mixtures thereof, is from 1% to 10% by weight of the total composition.

8. A composition according to claim 1 wherein the level of said cyclic terpene/sesquiterpene perfume, or mixtures thereof, is from 0.01% to 5% by weight of the total composition.

9. A composition according to claim 8 wherein the level of said cyclic terpene/sesquiterpene perfume, or mixtures thereof, is from 0.01% to 3% by weight of the total composition.

10. A composition according to claim 8 wherein the level of said cyclic terpene/sesquiterpene perfume, or mixtures thereof, is from 0.01% to 1% by weight of the total composition.

11. A composition according to claim 1 wherein said surfactant is selected from the group consisting of cationic surfactant, nonionic surfactant, anionic surfactant, zwitterionic surfactant and/or amphoteric surfactant, and is present up to a level of 50% by weight of the total composition.

12. A composition according to claim 1 wherein said surfactant is selected from the group consisting of cationic surfactant, nonionic surfactant, anionic surfactant, zwitterionic surfactant and/or amphoteric surfactant, and is present at a level of from 0.1% to 20% by weight of the total composition.

13. A composition according to claim 11, wherein said surfactant is a cationic surfactant or mixtures thereof.

14. A composition according to claim 11, wherein said surfactant is a thickening surfactant system comprising a cationic surfactant or mixtures thereof and an amine oxide having the formula $R_1R_2R_3NO$, wherein $R_1$ is a $C_6$ to $C_{10}$ alkyl group, and $R_2$ and $R_3$ are independently alkyl groups of from 1 to 4 carbon atoms, and wherein the composition has a viscosity of more than 100 cps at 20° C., when measured with a Brookfield viscometer at 60 rpm with a spindle n° 2.

15. A composition according to claim 14 wherein said composition has a viscosity of from 150 cps to 1500 cps at 20° C., when measured with a Brookfield viscometer at 60 rpm with a spindle n° 2.

16. A composition according to claim 1 wherein said composition has a pH of from 0 to 0.7.

17. A process of treating a hard-surface wherein a composition according to claim 11 is used.

18. A process of treating a hard-surface according to claim 17 wherein said hard-surface is a toilet bowl.

19. A process of treating a hard-surface wherein a composition according to claim 13 is used.

20. A process of treating a hard-surface according to claim 19 wherein said hard-surface is a toilet bowl.

21. A process of treating a hard-surface wherein a composition according to claim 14 is used.

22. A process of treating a hard-surface according to claim 21 wherein said hard-surface is a toilet bowl.

23. A composition according to claim 1 wherein the perfume is cedrol.

24. A composition according to claim 1 wherein the perfume is pinocarveolus.

25. A composition according to claim 1 wherein the perfume is sesquiterpinic globulul alcohol.

26. A composition according to claim 13 wherein the source of active oxygen is a monopersulfate salt or mixture of monopersulfate salts.

27. A composition of claim 13 wherein the quaternary ammonium compound is one wherein one or two of the hydrocarbon groups linked to nitrogen are saturated, linear or branched alkyl groups of 6 to 30 carbon atoms, and wherein the other hydrocarbon groups linked to the nitrogen are independently substituted or unsubstituted linear or branched alkyl chains of from 1 to 4 carbon atoms, and wherein the counterion used in said quaternary ammonium compound is methyl sulfate or methylsulfonate.

28. A composition of claim 14 wherein the quaternary ammonium compound is one wherein one or two of the hydrocarbon groups linked to nitrogen are saturated, linear or branched alkyl groups of 6 to 30 carbon atoms, and wherein the other hydrocarbon groups linked to the nitrogen are independently substituted or unsubstituted linear or branched alkyl chains of from 1 to 4 carbon atoms, and wherein the counterion used in said quaternary ammonium compound is methyl sulfate or methylsulfonate.

* * * * *